(12) United States Patent
Albert

(10) Patent No.: US 8,110,693 B2
(45) Date of Patent: Feb. 7, 2012

(54) METHOD AND DEVICE FOR DISSOLVING SOLIDS IN LIQUIDS

(76) Inventor: Gert Albert, Brunsbuttel (DE)

( * ) Notice: Subject to any disclaimer, the term of this patent is extended or adjusted under 35 U.S.C. 154(b) by 705 days.

(21) Appl. No.: 12/295,785

(22) PCT Filed: Mar. 27, 2007

(86) PCT No.: PCT/EP2007/002667
§ 371 (c)(1),
(2), (4) Date: Oct. 2, 2008

(87) PCT Pub. No.: WO2007/115672
PCT Pub. Date: Oct. 18, 2007

(65) Prior Publication Data
US 2010/0152471 A1    Jun. 17, 2010

(30) Foreign Application Priority Data
Apr. 7, 2006    (DE) .......................... 10 2006 016 398

(51) Int. Cl.
*C07F 5/06* (2006.01)
*B01J 8/08* (2006.01)

(52) U.S. Cl. .......................... 556/182; 422/209; 568/840

(58) Field of Classification Search .................. 556/182; 568/840; 422/209
See application file for complete search history.

(56) References Cited

U.S. PATENT DOCUMENTS
4,856,909 A    8/1989    Mehta et al.

FOREIGN PATENT DOCUMENTS

| | | |
|---|---|---|
| CH | 74735 | 9/1917 |
| DE | 291370 | 6/1915 |
| DE | 624373 | 1/1936 |
| DE | 714691 | 12/1941 |
| DE | 39 23 514 | 1/1991 |
| DE | 93 02 646 | 7/1993 |
| EP | 0 111 115 | 6/1984 |
| EP | 0 790 859 | 8/1997 |
| EP | 0 946 276 | 10/1999 |
| EP | 1 417 998 | 5/2004 |
| EP | 1417998 | 5/2004 |
| WO | WO 96/14150 | 5/1996 |
| WO | WO 98/19785 | 5/1998 |

OTHER PUBLICATIONS

International Search Report issued in corresponding International application No. PCT/EP2007/002667 mailed Aug. 13, 2007.

*Primary Examiner* — Porfirio Nazario Gonzalez
(74) *Attorney, Agent, or Firm* — Lempia Summerfield Katz LLC

(57) ABSTRACT

The invention relates to a method and device for dissolving solid bodies with a liquid, in particular for bringing solid bodies of different shapes and sizes, but mainly very course bodies, in contact with liquids, in order to dissolve them by a chemical reaction or dispersion. The device comprises a closed container (1) that is partially filled with the liquid and into which the solid bodies are introduced before being received inside the container (1) into a basket (2) that is movable relative to the container (1), and the solid bodies inside the basket (2) are brought into contact with the liquid. For the solid bodies to be introduced more easily, quickly and also more uniformly into the basket inside the container (1), in order to be dissolved, the basket (2) is suspended inside the container (1) in an oscillating manner, such that it can be moved back and forth, after it is filled with a bulk load of solid bodies, in alternating directions of rotation relative to the container (1).

19 Claims, 2 Drawing Sheets

METHOD AND DEVICE FOR DISSOLVING SOLIDS IN LIQUIDS

RELATED APPLICATION DATA

This U.S. National Phase Application is based on and claims priority benefit of international application no. PCT/EP2007/002667 filed on Mar. 27, 2007 which claimed priority benefit of German national patent application no. 10 2006 016 398.2 filed on Apr. 7, 2006.

BACKGROUND

1. Field of the Disclosure

The invention concerns a device and a method according to the main clause of claims 1 and 16 and in particular for bringing into contact and dissolving of mainly very coarse solids of different shape and size in a fluid, in order to dissolve them by chemical reaction or dispersion.

2. Description of the Related Art

A device for bringing into contact of solid reactants with liquids is known from EP 0 790 859 B1, that comprises a container that can be filled with the liquid and a sieve drum that is built into the container and closed on all sides, that is rotatable on a hollow shaft around 360° and is immersed into a vat that can be lowered. The sieve drum in the known device can be loaded with the solid reactants exclusively through its hollow shaft. This has disadvantage that the maximum amount of solid used and the size of the pieces are limited by the shaft diameter. The fact that the hollow shafts, which are mainly occupied by conveyor systems, are narrow leads to the fact that the liquid reactant must be fed into the vat below the drum, and it must flow through the wall of the drum in order to come into contact with the solid. This occurs only partially and has a considerable adverse impact on the performance of the device because of a deficiency of the liquid reactants in the reaction zone within the sieve drum. In addition, when the drum has to be inspected, expensive dismounting of large wall areas of the drum is required. Furthermore, the relatively large shaft diameters reduce the reaction space of the device greatly, so that the volume that is usable for the reaction is definitely less than 50% of the drum volume. Moreover, the entire bulk load falls into the drum only at two points, namely in the area of the front disks, so that the available reaction space is naturally filled nonuniformly, which again results in a reduction of capacity. Moreover, in this device the drum diameter must be increased in part just so that the gases and vapors that are formed in the reaction chamber can flow without any problem through the upper sieve surface that is not in contact with the liquid.

A device is known from EP 0 946 276 in which, using a rotary grate that moves in a briskly boiling vat, large solid pieces can be brought into contact with a liquid. The disadvantage of this device is the very high energy consumption as a result of the extremely large amount of fluid to be circulated for the briskly boiling layer. The economy of this construction arises mainly when it is used to re-equip reactors from Patent EP 0 111 115.

SUMMARY

The task of this invention is to avoid the outlined disadvantages, to make it possible to introduce the solids more simply, more rapidly and more uniformly into the basket located in the container and at the same time to reduce the running operating costs and the specific manufacturing expenditure for a solid-liquid reactor while keeping the safety unchanged.

The task set is solved according to the invention by the characteristics given in the characterizing part of claims 1 and 16.

Accordingly, a preferably oval or cylindrical basket open on the top serves for holding the solids, and in the surrounding container, which is closed on all sides and filled with liquid to about 50%, this basket is suspended so that it oscillates, preferably around its generally horizontal gravity axis.

The solids, mostly several kilograms in weight, are introduced into the basket as bulk load. The wall of the basket allows full transmission of liquids and gases in both directions, but not of the solids, the size of which exceeds the selected size of the openings in the wall.

The two solid ends of the axis or shaft for the oscillating suspension of the basket are guided to the outside through the container wall through seals. At the ends of the shaft counterweights that can be shifted on rods are attached, and on one side a basket drive motor is also arranged.

The solids in the form of bulk load are introduced through one or several material sluices that are attached in a fixed manner at the highest point of the surrounding container. In or near the zero or rest position of the oscillating basket (opening on top), the solids can fall from the sluices directly into this, in a uniformly distributed manner. Costly transporting parts in hollow shafts including additional seals against rotating parts are absent.

The introduction of the reaction fluid as well as also any condensate reflux in the case of exothermic reactions also occurs from the top directly into the reaction area of the basket.

As a result of the oscillating movement of the basket—possibly also supported by blade strips—continuous movement of the solids occurs and optimum contact with the liquid as well as their mixing in the reaction/treatment area is achieved.

An embodiment of the invention provides that the upper basket opening represents approximately 20% of its total surface area and the total angle of rotation of the basket from one end position to the other is about 60° (+30° to −30° with respect to the vertical).

This large opening ensures that unlimited amounts of gas and steam can flow out at any time and without any hindrance away from the reaction area.

Another embodiment of the invention provides that when the sluices are ready to feed, the oscillating basket stops for a short moment in the zero or rest position and then unhindered introduction of the material into the basket can occur.

Another embodiment of the invention provides that two or more sluices are used for increasing the throughput as well as for rapid and optimum distribution of the bulk load over the length of the basket.

Another embodiment of the invention provides that in the area of the bulk load feeding locations a distributor is applied in each of the baskets in the shape of a double wedge, so that as a result a very uniform material loading in the basket can be achieved to start with. Moreover, as a result of this distributor, the stress on the basket wall by the gravitational forces of the bulk load material is reduced significantly because the pieces are deviated horizontally to start with. A separate all-around protection against impact inside the basket therefore becomes unnecessary and saves cost.

The direct route from the sluice exit into the basket also permits feeding of bulk load, for example, pressed scrap or large chip packets of all types and of a multiple number of dimensions, etc.

In order to make continuous introduction of liquid into the reaction/treatment zone possible, another embodiment of the invention provides that a sufficiently broad strip next to the basket opening be delineated by a raised edge so as to create a temporary liquid storage (intermediate buffering) on the part of the transmitting wall surface that is located just below the liquid inlet locations, when the basket moves from the zero or rest position into the extreme positions and back again.

Another embodiment of the invention provides for a balancing of the oscillating basket through the use of two counterweights that are arranged outside the container at the ends of the shafts and can be shifted radially. In each position of the basket, the weights are set hydraulically so that the torque resulting from the filling of the basket is compensated and thus, in continuous operation, an absolute minimum of basket drive power is achieved.

Another embodiment of the invention provides that the posts of the reactor container are formed as closed receiving containers and are available for holding reactor liquid in case the reaction—for whatever reason—has to be interrupted spontaneously or temporarily. No additional energy is required for letting the reactor liquid flow into such containers, since the liquid can flow into the posts as a result of their gravitational force.

The liquid level in the reaction container is chosen through level regulation corresponding to the reaction volume requirement and the desired oscillating amplitude.

Rapidly emptying armatures and receiving containers as support for the reactor container make a special vat that can be lowered inside the container superfluous.

With this invention reactors according to EP 0 790 859 B1 can be converted to provide greater throughput, allow larger and more bulky pieces, and to provide a reduced maintenance expenditure.

BRIEF DESCRIPTION OF THE DRAWINGS

The invention will now be explained in more detail with the aid of the drawing.

The two

DETAILED DESCRIPTION OF THE DISCLOSURE

Figure 1:
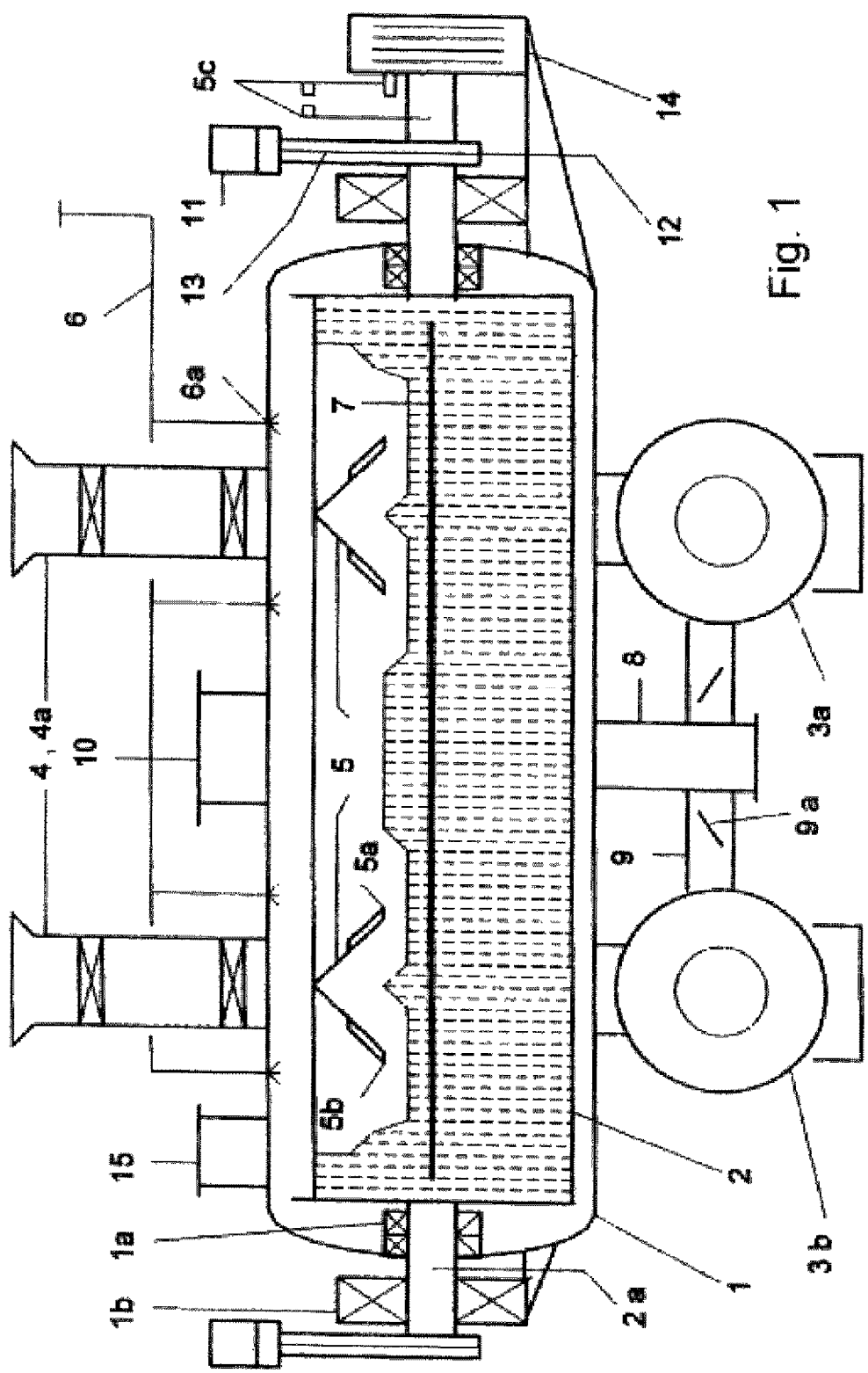
FIGS. 1 and 2 show partially cut side or front views of a reactor for the manufacture of aluminum, magnesium or mixed alcoholates by dissolving coarse pieces of aluminum/magnesium in hexanol.
Figure 2:
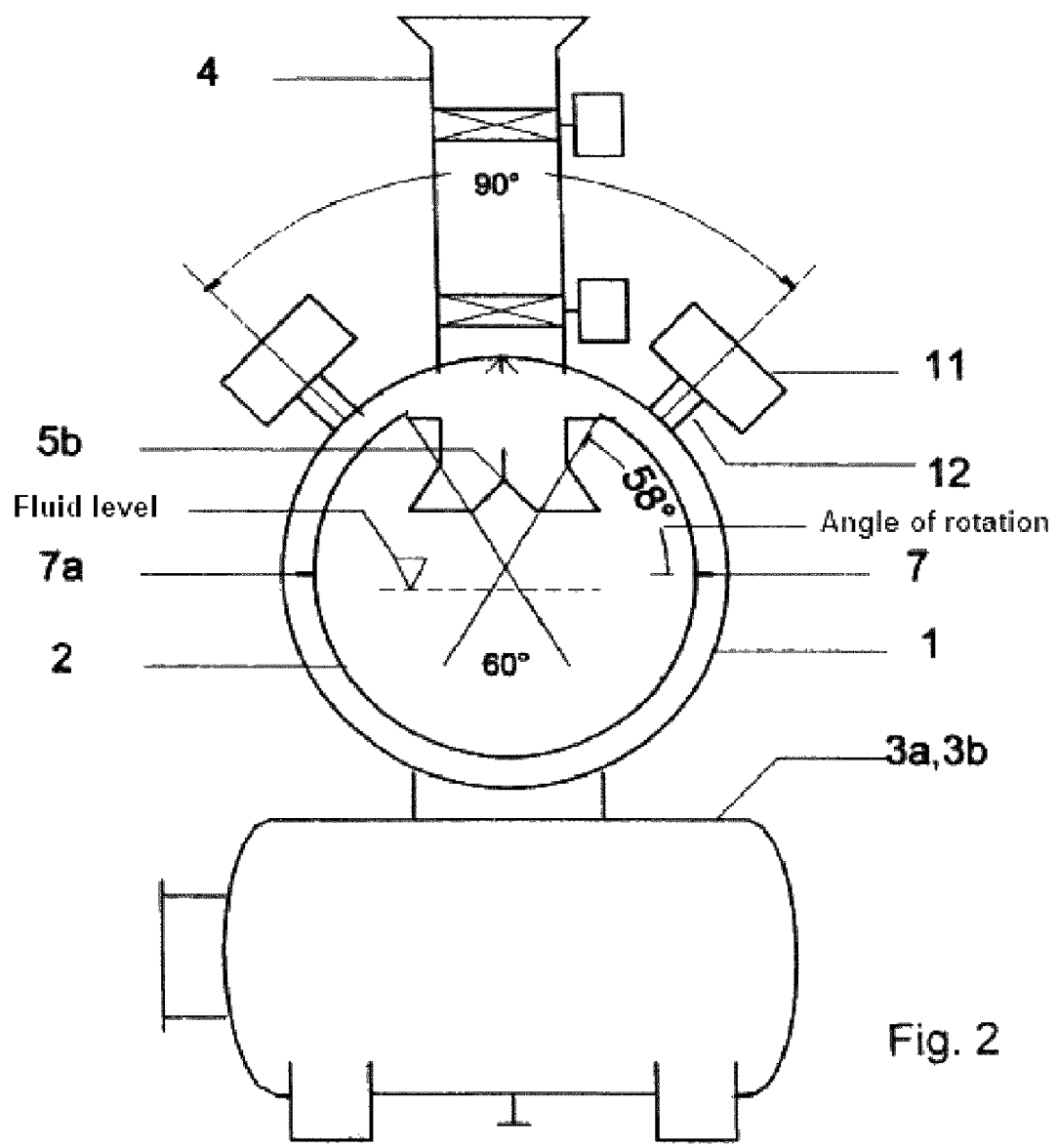

The oscillating basket (2), which is open on top, is located in the horizontal reaction container (1) and this basket is suspended on a shaft (2a) so that it oscillates around a horizontal rotational axis. The shaft (2a) is guided toward the outside through seals (1a) and is supported on bearings (1b) on the front covers of the container (1).

The reaction container rests on also horizontal closed liquid receiving containers (3a) and (3b) which in turn are set on a reinforced concrete or steel base.

The solid material is introduced into the oscillating basket (2) through sluices (4, 4a) which are not described in detail, and which are arranged on the uppermost part of the reactor container (1) and prevent exit of gases and steam from the container (1).

When solids are in the sluices (4, 4a) and the sluices (4, 4a) are ready for emptying, the oscillating basket (2) stops, controlled by contacts (5c) for a few seconds in its zero or rest position, so that the bulk load leaving the sluices (4, 4a) can fall into the basket due to gravity.

Material distributors (5) are installed in the baskets centrally, under the sluices. They consist of three wedges connected to one another, namely the main wedge (5) and two secondary wedges (5a, 5b) that are located at the end of the sliding surfaces (5). As a result of this, the solid streams entering through the sluices are distributed into four partial streams and are placed in the basket at an optimum distance from one another.

The liquid is introduced through a distributor tube (6) attached at the top on the reactor mantle. When the basket opening during the oscillating movement exceeds the outlet opening (6a) for a short moment, the entire fluid flows onto the wall area delineated by the raised edges (7, 7a) on the right and left of the basket opening and from there, with only a slight delay, directly into the reaction zone.

The product is removed through the reactor container sump (8). From this, rapid emptying lines (9) branch into receiving containers (3a, 3b). The locking armatures (9a), which are closed during normal operation, are equipped with an emergency opening device, for example spring activated, in case of power failure, so that the reaction of the solids with the liquid can be discharged rapidly and without pumping into the receiving container (3a, 3b) by opening the armatures (9a).

Reaction products—for example gases or vapors from a boiling condenser in the case of exothermic reactions—flow from the inside of the basket through a connection (10) out of the reaction container (1). Reflux of condensed vapors returns directly into the basket through (6, 6a).

Counterweights (11) for balancing the basket due to its filling during operation with solids, can be displaced radially on extension arms (12) that are inclined by about 45° and that are solidly connected to the outer ends of the shaft. The displacement is done with hydraulic cylinders (13) which in turn are operated by a pumping aggregate not shown here.

The oscillating drive of the basket (2) in alternating directions of rotation is done with the aid of a drive motor (14), the direction of rotation of which can be reversed, and which is equipped with a brake.

The basket design with inserts permits arbitrary introduction of solids with regard to shape, amount and size with simultaneous optimum and protective distribution in the reaction chamber. The same applies to the introduction of liquid into the reaction zone, as a result of which ideal reaction conditions are created.

The discharge of reaction gases and vapors is always unlimited and unhindered, and immediate energy-independent rapid emptying of the reaction container is also ensured.

Entry into the reactor can occur in the zero or rest position of the basket (2) through a manhole (15).

The invention claimed is:

1. A device for the production of aluminum, magnesium or aluminum/magnesium mixed alcoholates by reaction of predominantly very coarse solids made of aluminum or magnesium with a liquid consisting of $C_1$-$C_{12}$ alcohols with dissolution of the solids, the device comprising:
   a reactor container that can be filled with the liquid; and
   a basket that is open on top and is arranged within the container for holding the solids, whereby the basket is suspended on a horizontally directed shaft so that it can oscillate to produce an oscillating movement within the container, whereby the basket has a filling opening, which, in a rest position of the basket, is arranged below at least one loading sluice arranged on the top side of the container, and whereby the basket has a material distributor in the region of the filling opening in order to deflect and distribute the solids in the basket.

2. A device according to claim 1, wherein the shaft is led to the outside through sealed wall openings of the container.

3. A device according to claim 1, wherein the shaft is provided, outside the container, with radially displaceable counterweights.

4. A device according to claim 1, wherein the shaft is supported outside the container in rotary bearings and is connected to a rotary drive.

5. A device according to claim 4, wherein the rotary drive comprises a drive motor with reversible direction of rotation and a locking brake.

6. A device according to claim 4, wherein a position switch is arranged outside the container for control of the rotary drive for stopping or changing the direction of the oscillating movement of the basket.

7. A device according to claim 1, wherein the filling opening extends essentially throughout the entire length of the basket and has an opening angle of between 45 and 90 degrees in the direction of rotation of the basket.

8. A device according to claim 7, wherein the opening angle is about 60 degrees.

9. A device according to claim 1, wherein the liquid can be introduced into the container from the top.

10. A device according to claim 1, wherein a wall of the basket allows gases, vapors and liquids to pass in both directions, but does not allow passage of solid pieces.

11. A device according to claim 1, wherein the basket is provided with raised edges on its outer side to catch liquid that hits the basket during its oscillating movement near the filling opening.

12. A device according to claim 1, wherein the container is carried by hollow feet that are separated by valves from the inside of the container and permit any time, even in an emergency, the complete emptying of the container into the feet.

13. A method for the production of aluminum, magnesium, or aluminum/magnesium mixed alcoholates by dissolving predominantly very coarse solids consisting of aluminum or magnesium with a liquid consisting of $C_1$-$C_{12}$ alcohols, the method comprising:
   introducing the solids into a reaction container filled partially with the liquid;
   holding the solids within the container in a basket that is displaceable with respect to the container; and
   bringing the solids in the basket into contact with the liquid, whereby the solids are introduced from the top both into the container and also into the basket though a filling opening, whereby the liquid is introduced directly into the basket from the top, and whereby the solids are moved around and are mixed with the liquid by an oscillating movement of the basket.

14. A method according to claim 13, wherein, in a rest position, the basket is loaded from above with the solids through a filling opening.

15. A method according to claim 14, wherein the solids are deviated during loading of the basket in several directions in the area of the filling opening.

16. A method according to claim 13, wherein counterweights are shifted hydraulically on a shaft that carries the basket to compensate for fluctuating torques during the oscillating movement of the basket in the radial direction with respect to the shaft.

17. A method according to claim 13, wherein the solids in the basket are sprayed with the liquid and are immersed into the liquid.

18. A method according to claim 13, wherein the solids in the basket are sprayed with the liquid or are immersed into the liquid.

19. A method according to one of claim 13, characterized by the fact that the dissolution of the solids is interrupted by discharging the liquid from the container (1).

* * * * *